(12) United States Patent
Fuerst et al.

(10) Patent No.: US 11,007,031 B2
(45) Date of Patent: May 18, 2021

(54) SETUP OF SURGICAL ROBOTS USING AN AUGMENTED MIRROR DISPLAY

(71) Applicant: Verb Surgical Inc., Mountain View, CA (US)

(72) Inventors: Bernhard Adolf Fuerst, Sunnyvale, CA (US); Pablo E. Garcia Kilroy, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 1 day.

(21) Appl. No.: 16/103,864

(22) Filed: Aug. 14, 2018

(65) Prior Publication Data

US 2020/0054412 A1 Feb. 20, 2020

(51) Int. Cl.
*A61B 34/30* (2016.01)
*A61B 34/20* (2016.01)
*A61B 90/00* (2016.01)
*A61B 17/00* (2006.01)

(52) U.S. Cl.
CPC ............ *A61B 90/361* (2016.02); *A61B 17/00* (2013.01); *A61B 34/20* (2016.02); *A61B 34/30* (2016.02); *A61B 2017/00115* (2013.01); *A61B 2034/2057* (2016.02); *A61B 2034/2065* (2016.02); *A61B 2090/365* (2016.02); *A61B 2090/3618* (2016.02); *A61B 2090/373* (2016.02)

(58) Field of Classification Search
CPC .............................................. A61B 34/20–32
See application file for complete search history.

(56) References Cited

U.S. PATENT DOCUMENTS

| 2002/0140708 | A1 | 10/2002 | Sauer | |
| 2009/0177081 | A1* | 7/2009 | Joskowicz | A61B 90/13 600/426 |
| 2014/0081659 | A1* | 3/2014 | Nawana | G16Z 99/00 705/3 |
| 2015/0099252 | A1* | 4/2015 | Anderson | G09B 19/003 434/257 |
| 2016/0257000 | A1 | 9/2016 | Guerin et al. | |
| 2016/0324580 | A1* | 11/2016 | Esterberg | A61B 34/10 |
| 2017/0049517 | A1* | 2/2017 | Felder | A61B 34/37 |
| 2017/0172674 | A1* | 6/2017 | Hanuschik | A61B 90/13 |
| 2017/0239000 | A1* | 8/2017 | Moctezuma de la Barrera | A61B 17/154 |
| 2017/0312032 | A1 | 11/2017 | Amanatullah et al. | |

(Continued)

OTHER PUBLICATIONS

Navab, Nassir, et al. "First deployments of augmented reality in operating rooms." Computer 45.7 (2012): 48-55. (Year: 2012).*

(Continued)

*Primary Examiner* — Ryan McCulley
(74) *Attorney, Agent, or Firm* — Womble Bond Dickinson (US) LLP

(57) ABSTRACT

Assisting robotic arm setup in a surgical robotic system using augmented reality can include capturing a live video of a user setting up a robotic arm in a surgical robotic system. A visual guide representing a target pose of the robotic arm can be rendered onto the live video, resulting in an augmented live video for guiding the arm setup. The augmented live video can be displayed to the user while the user is following the visual guide to set up the robotic arm. The captured live video can be continuously processed to determine whether the robotic arm has reached the target pose.

19 Claims, 9 Drawing Sheets

(56) References Cited

U.S. PATENT DOCUMENTS

2018/0140309 A1*  5/2018  Fouts ..................... A61B 34/10
2019/0000569 A1*  1/2019  Crawford ............... A61B 34/30
2019/0038362 A1*  2/2019  Nash ...................... A61B 34/20

OTHER PUBLICATIONS

PCT International Search Report and Written Opionion dated Apr. 17, 2019 for related PCT Application No. PCT/US2018/048861 11 Pages.
International Preliminary Report on Patentability for International Application No. PCT/US2018/048861 dated Feb. 25, 2021, 8 pages.

* cited by examiner

SETUP OF SURGICAL ROBOTS USING AN AUGMENTED MIRROR DISPLAY

CROSS-REFERENCE TO RELATED APPLICATIONS

None.

TECHNICAL FIELD

This invention relates generally to surgical robotic systems, and more specifically to new and useful systems and methods for providing augmented reality surgical robotic environments.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more tools and at least one camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. A robotic arm may, for example, support at its distal end various devices such as surgical end effectors, imaging devices, cannulae for providing access to the patient's body cavity and organs, etc.

MIS may be performed with non-robotic or robotic systems. Conventional robotic systems, which may include robotic arms for manipulating tools based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

Robotic surgical systems, for example, those used in MIS, can have three or more degrees of freedom. This creates a near unlimited number of poses for the robotic arms and, as the degrees of freedom increase, so does the complexity of setting up the robots. Medical staff and personnel typically pose the robotic arms prior to the start of surgery. Importantly, the robotic arms must be in the correct pose relative to a patient; otherwise, complications can come about during surgery.

Thus, the setup and correct configuration of robotic arms is a complex task. The proper pose of robotic arms can be difficult to illustrate to medical staff. Similarly, it may be difficult for the staff, even when looking at various illustrations of the same pose, to fully visualize that pose in real space. The spatial relationship between the staff member's body, real objects in the surgical environment (for example, tool stands, stools and lights), and the target pose is lost.

In addition, in moving the surgical robots from one pose to another pose or a target pose, there may be obstacles in the way, such as other surgical robots, lamps, tools, trays, or other objects typical in such an environment. Again, it is difficult to visualize what these obstacles are because the desired pose of the surgical robot is not readily evident, nor is the path between the current pose and the target pose obvious.

In addition, even after medical personnel have completed setup of the robotic arm; it is not evident whether the robotic surgical arm is actually in the correct pose. In other words, there should be an objective manner in verifying that the robotic surgical arm is posed correctly for a given procedure, perhaps taking into account the size and shape of the patient, the type of robotic surgical arm, the type of distal end devices used, the point or points of entry into a patient, and other considerations.

Thus it is desirable to develop a system that can help setup surgical robots in a reliable and verifiable manner that can be tailored for different operations, patients and tools.

SUMMARY

Generally, a system for guiding arm setup in a surgical robotic system using augmented reality can include a camera and a processor (for example, an augmented reality (AR) processor). The camera can be configured to capture a live video of a user setting up a robotic arm in a surgical robotic system. The AR processor can be configured to receive the live arm setup video captured by the camera, render a virtual surgical robotic arm in a target pose onto the live arm setup video, resulting in an augmented live video for guiding the arm setup, and stream the augmented live video to a display to visually guide the user through arm setup to the target pose.

In another aspect, the AR processor is further configured to process the live setup video continuously to determine whether the robotic arm is at the target pose as represented by the virtual robotic arm, and trigger an indication when the robotic arm is overlaid on the virtual robotic arm at the target pose. This provides feedback as to whether the task of moving the robotic arm into the target pose is complete.

It is to be understood that the camera and AR processor capture, process, and display the augmented surgical environment video while the user is setting up and watching the display, so that the user can properly setup the surgical robot or robots. In this manner, medical staff can view the display while arranging robotic arms for robotic surgical procedures. The medical staff member will gain an improved understanding of spatial relations between the real robotic arm and other real objects, as well as have a visual guide, e.g. the virtual surgical robotic arm in the target pose, for arranging the robotic arm.

DETAILED DESCRIPTION

Figure 1:
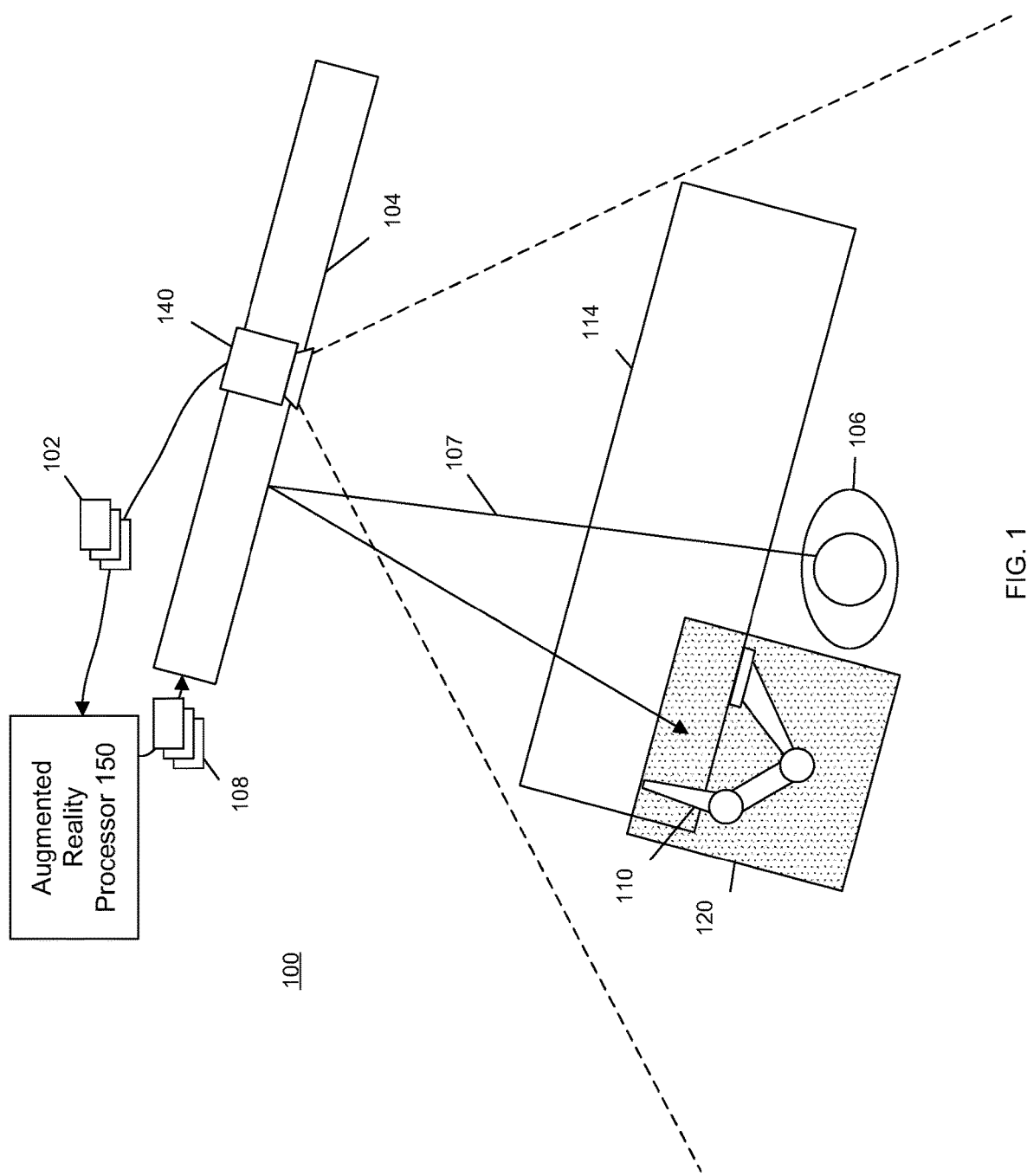
FIGS. 1 and 2 show embodiments of a system for assisting in the setup of surgical robotic arms.

Examples of various aspects and variations of the invention are described herein and illustrated in the accompanying drawings. The following description is not intended to limit the invention to these embodiments, but rather to enable a person skilled in the art to make and use this invention.

The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosures.

Reference in the specification to "one embodiment" or "an embodiment" means that a particular feature, structure, or characteristic described in conjunction with the embodiment can be included in at least one embodiment of the disclosure. The appearances of the phrase "in one embodiment" in various places in the specification do not necessarily all refer to the same embodiment.

A "robotic arm" or "robot arm" or "robotic surgical arm" or other variations of such are used herein to describe movable jointed and motorized members with multiple degrees of freedom that can hold various tools or appendages at distal ends. Typical systems include the da Vinci(r) Surgical System which can be used for minimally invasive surgery (e.g., urologic surgical procedures, general laparoscopic surgical procedures, gynecologic laparoscopic surgical procedures, general non-cardiovascular thoracoscopic surgical procedures and thoracoscopically assisted cardiotomy procedures).

A "real surgical environment" as used herein describes the local physical space of the setup, which can include robotic arms, mounts, surgical tables, lamps, trays, medical personnel, the room and objects in the room.

A "target pose" as used herein describes a desired pose of the surgical robotic arm. Thus, a virtual robotic arm or abstraction of such can rendered to an augmented reality live video in a "target pose". An AR processor can determine when a real robotic arm is in the same pose as the virtual robotic arm, or within an allowed tolerance (capable of being determined and defined by one skilled in the art) or the target pose. The "target pose" can also be a range of poses, for example, more than one pose. Robotic arms can include a plurality of members connected at different types of joints (for example, rotational, revolving, twisting, orthogonal or collinear). Each pose can be described as a unique configuration of the relative or absolute positions and/or orientations of each member of a robotic arm. Thus, each robotic arm can assume numerous poses based on the orientations, positions, and extensions of the robotic members, similar to how a human model can strike various different poses by moving, for example, a head, neck, arm, leg, and/or hips. Furthermore, the pose can include a location of the robotic arm in a room. For example, the location of the robotic arm can be based on a location (relative or absolute) of a base attachment of the robotic arm. The pose can include the positions and orientations of each member, and the location of the robotic arm as a whole. A position can be described as where a member is. The orientation can be described as a direction that the member (or an axis of the member) is pointing and the member's rotation.

A "virtual robotic arm" as used herein describes a computer generated model of a robotic arm rendered over the captured video of a user setup. The "virtual robotic arm" can be a complex 3D model of the real robotic arm. Alternatively or additionally, a "virtual robotic arm" can include visual aids such as arrows, tool tips, or other representation relating to providing pose information about a robotic arm such as a geometrically simplified version of the real robotic arm.

A "live" video, as used herein, describes video data that is captured and processed while the actions in the video are happening, or with a minimal delay, as allowed by the system software and hardware (for example, delays caused by transmission, processing, and buffering). Similarly, to "stream" a video, as used herein, describes transmitting video data to be processed or displayed live.

System and Display

Figure 3:
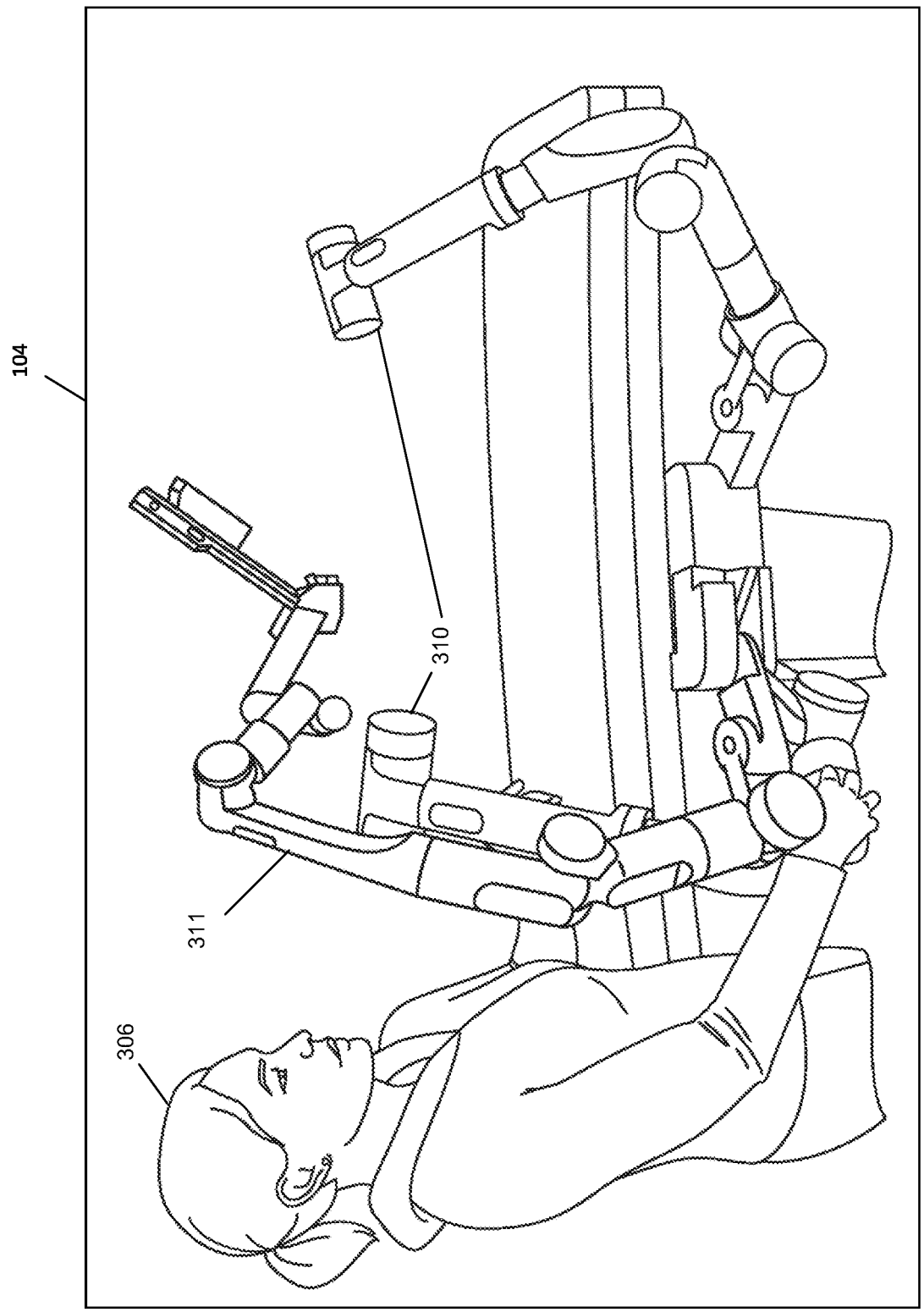
FIG. 3 illustrates the virtual reality mirror in one embodiment.
Figure 4:
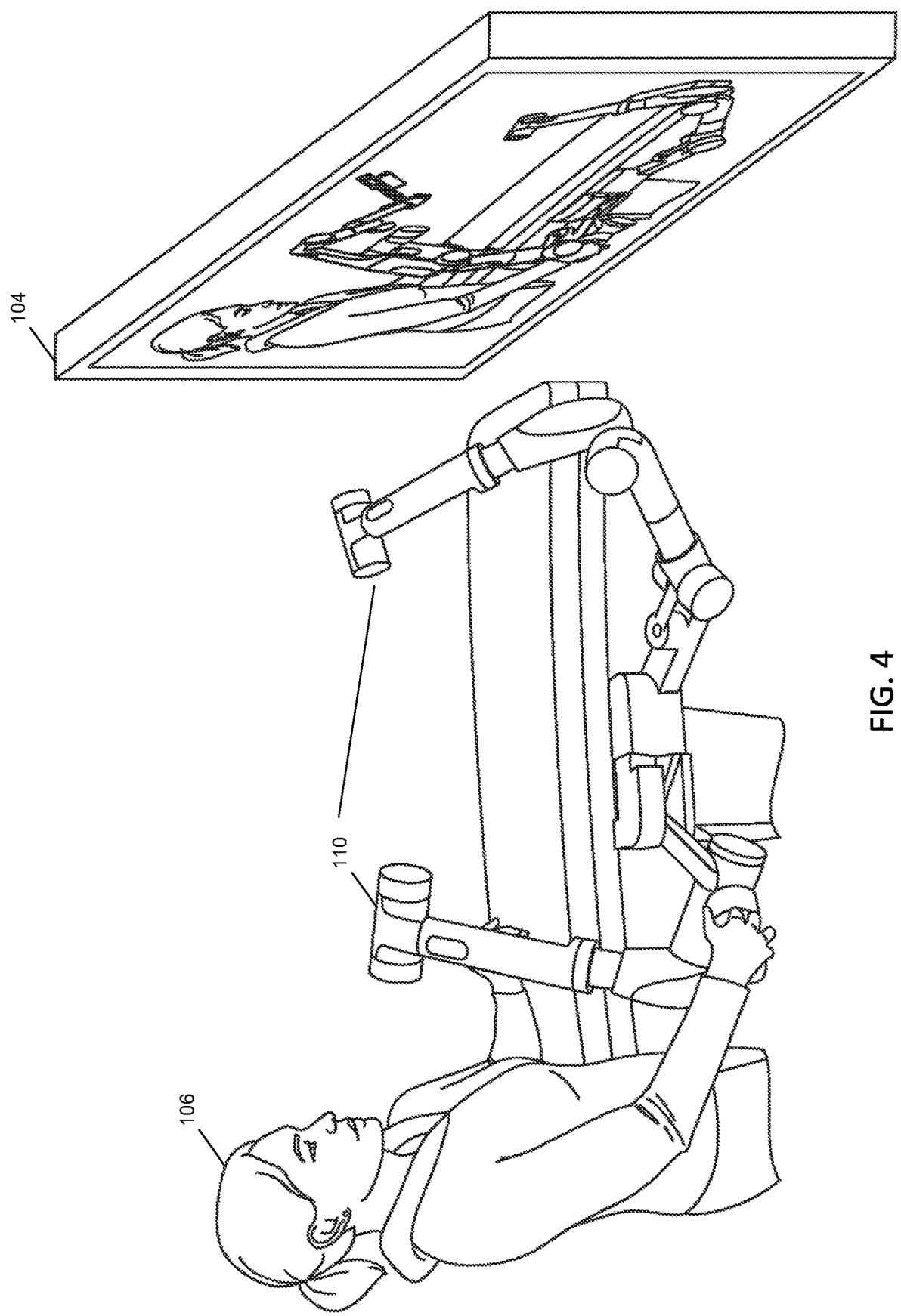
FIG. 4 illustrates the user viewing the augmented reality mirror through a display.

As shown generally in the schematic of FIG. 1, a robotic surgical system 100 for assisting in the setup of a surgical robotic arm or arms 110 in a surgical environment using a display 104 can include a camera 140, configured to capture video of a user 106 setting up the robotic arm 110 mounted on a surgical table 114 in a real surgical environment; an AR processor 150, configured to: receive the live arm setup video 102 captured by the camera; render a virtual surgical robotic arm that is in a target pose (as shown in FIGS. 3 and 4), onto the live arm setup video, resulting in a live augmented surgical environment video 108 for guiding the arm setup; and stream the live augmented video to a display 104; where the display is configured to display the augmented surgical environment video.

FIG. 3 shows the rendered augmented surgical environment video on a display 104. The user 306 is shown moving one of the real robotic arms 310. The AR processor has rendered the virtual robotic arm 311 giving a visual indicator to the user for guiding the real robotic arm 310 to match the target pose of the virtual robotic arm. The AR processor renders the virtual robotic arm at the same anchor/mount point as the real robotic arm 310, thus giving the real and virtual robotic arms a common anchored reference point.

FIG. 4 shows the user 106 manipulating the real robotic arm 110 while watching the live augmented surgical environment video on the display 104. In one aspect, augmented surgical environment can be displayed as a mirror image. For example, the system can flip or reverse the video images captured by the camera along a vertical axis of the video images, resulting in a mirror image video. The mirror image video can then be output to the display 104. In this manner, the system can provide a natural reflection like a mirror. In another aspect, the live augmented surgical environment is displayed from the point-of-view of the camera. The different camera views can be configured and selected, for example, based on user preference.

Robotic arms and Computer Vision

Figure 2:
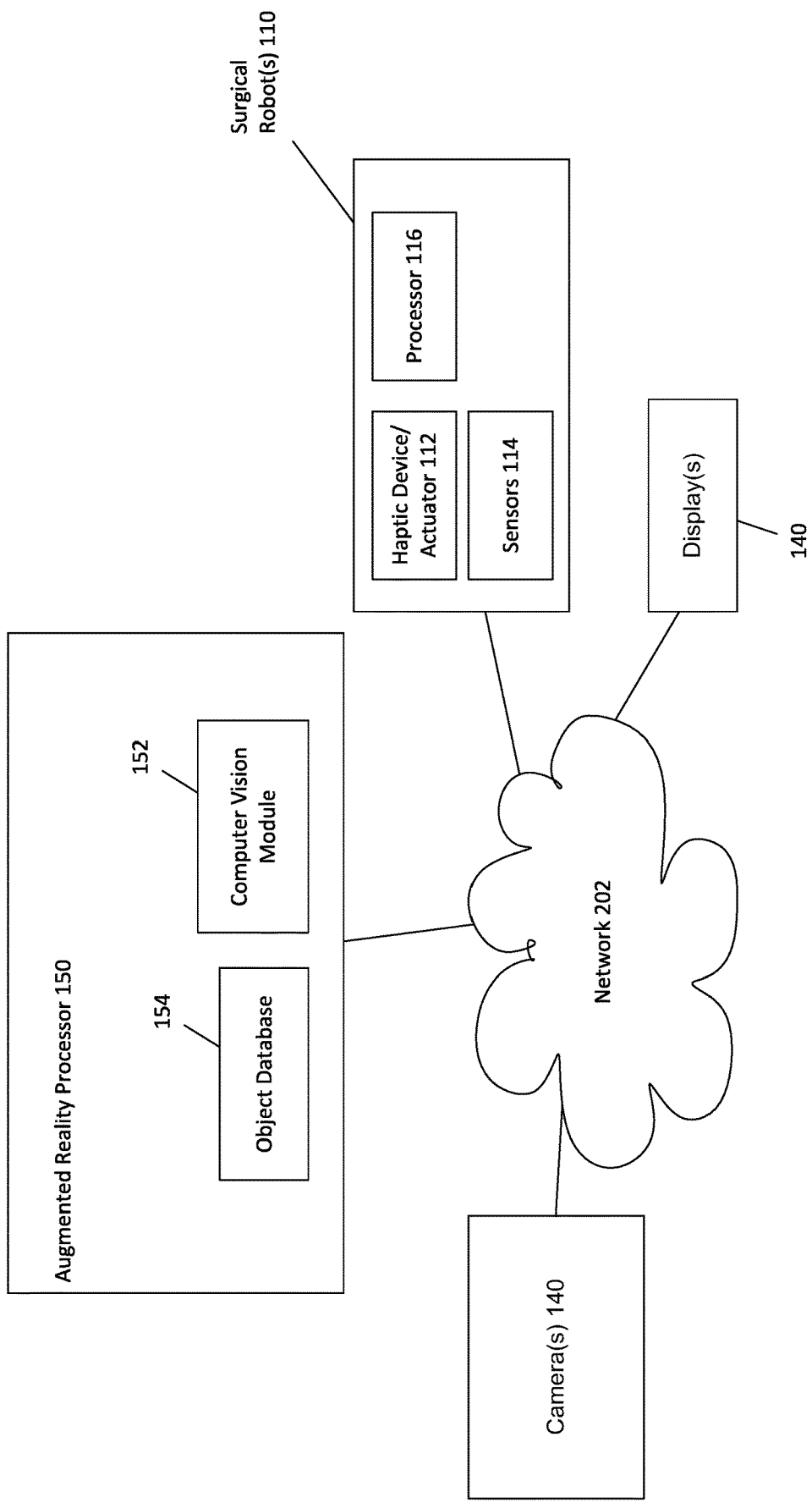

Referring now to FIG. 2, the AR processor can receive and process status messages from one or more robotic arms in the real surgical environment through the network 202. Each of the one or more robotic arms can have an associated module or processor 116 with communications, programmed logic, and memory, capable of gathering and organizing data from sensors 114 (for example, position sensors, accelerometers, etc.), and communicating the data to the AR processor 150. Thus, the AR processor 150 can receive status data from a real robotic arm in the real surgical environment, for example, the position/orientation (rotation, pitch angle, travel) of different members of the real robotic arm, or alert messages to determine if there is a problem with any of the robotic arms.

As shown in FIG. 2, the augmented reality processor 150 can include one or more database(s) 154 or having access to such a database through the network 202. The database(s) can include models of different robotic arms, poses for robotic arms, surgical tables, patient data, and data structures to correlate different poses of robotic arms to different surgical procedures, tables, and patients. The processor can thus be configured to identify a real surgical robotic arm and a surgical table by comparing and matching objects in the surgical environment with 3D models of tables and surgical robots stored in computer memory. Configuration files corresponding to different surgical procedures with robotic arms can be stored in memory and selected (for example, through a user interface) prior to or during setup.

As shown in FIG. 2, the system can include a database 154 stored in electronic memory, or having access to such a database through the network 202. The database can include one or more 3D models of robotic arms, each robotic arm being associated with one or more target poses and, a user interface configured to provide selectable options of the one or more 3D models of robotic arms and the associated target poses.

The AR processor can also include a computer vision module 152, configured to perform scene reconstruction, event detection, video tracking, object recognition, 3D pose estimation, learning, indexing, motion estimation, image restoration, and other known computer vision techniques based on the captured video. It can apply the 3D vision techniques described above to analyze the captured video and identify the surgical robot arms, the surgical table, the patient or dummy, the medical personnel, other objects, and orientations and positions of such, in the surgical environment. Alternatively, or additionally, the processor can identify and/or track objects (for example, the robotic arms and the surgical table) with 2D markers (for example, labels or stickers placed on the objects).

Target Pose

The AR processor can be configured to process the captured video to determine whether a pose of a real surgical robotic arm is at a target pose of the virtual surgical robotic arm; and trigger an indication when the pose of the real surgical robotic arm is at the virtual robotic arm. The determination can be made based on 3D object recognition, 3D pose estimation, and other techniques capable of being implemented by one skilled in the art of computer vision, to detect the pose of the real robotic arm in the captured video and then compare that pose to the target pose. In this regard, the processor can then determine whether the real robotic arm is at, or within a tolerance of, the target pose, shown by the computer generated virtual surgical robotic arm.

Figure 9:
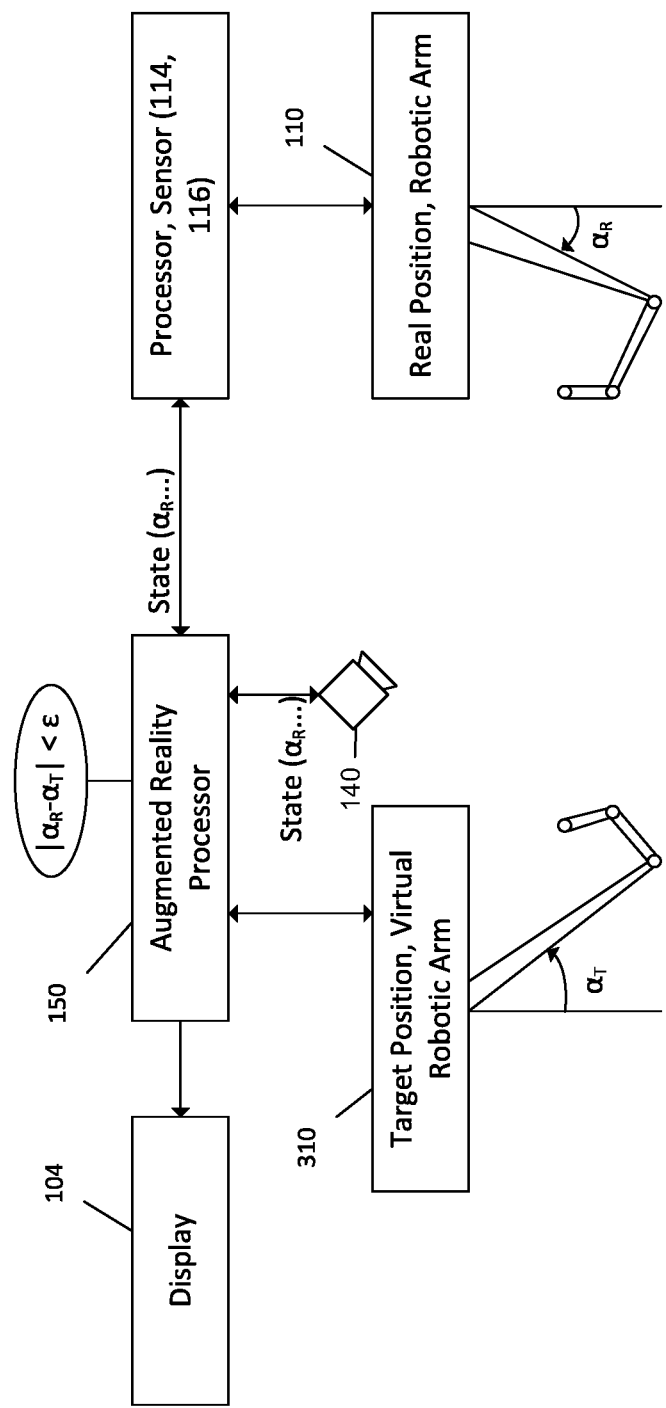
FIG. 9 shows a system that determines a target pose in one embodiment.

Referring to FIG. 9, in one aspect, a control system (for example, a processor 114 and sensors 116) of a robotic arm 110 can sense and calculate pose information of the robotic arm, or members of the robotic arm. The AR processor can receive the pose information, for example, an angle $\alpha_R$ of a member of the robotic arm relative to an axis or plane. The AR processor can compare the received pose information, for example, the angle $\alpha_R$, with a corresponding angle $\alpha_T$ of a corresponding member of the virtual robotic arm 310, relative to an axis or plane, to determine an error $\varepsilon$. If the error $\varepsilon$ is less than a determined tolerance, that member (of the robotic arm) can be determined to be at, or sufficiently overlaid upon, the target pose (as shown by the virtual robotic arm). Depending on the application (for example, the type of robotic arms used and the surgical operation), this process of comparing pose information can be repeated for a plurality or all members of the robotic arm, to determine if each member is within an error of the target pose. Upon such a determination, the AR processor generate an indication, for example, a visual indication rendered onto the live arm setup video, and display the augmented live video on display 104.

Additionally or alternatively, pose information of the robotic arm can also be determined by the AR processor based on the captured live arm setup video received from camera 140. The AR processor can determine pose information of the robotic arm in the captured live arm setup video using suitable techniques (for example, through computer vision and/or depth sensors).

Although FIG. 9 shows a comparison of angles, the determination of whether a robotic arm is at a target pose can include comparisons of additional pose information of robotic members and combinations thereof. For example, the pose information can also include rotational orientations (for example, for rotating or twisting members) and travel lengths (for example, for extending or telescoping members). Pose information can be based on position sensors, linear positional sensors, displacement sensors, magnetic sensors, controller data, encoders, and other equivalent robotic sensing techniques.

Indicators

For example, FIG. 3 shows the user 306 manipulating the robotic arm 310 to match the target post of the virtual robot 311. Once the AR processor determines that the real robotic arm is at or within a tolerance of the target pose, the processor can respond with an indication/notification to the user.

Figure 5:
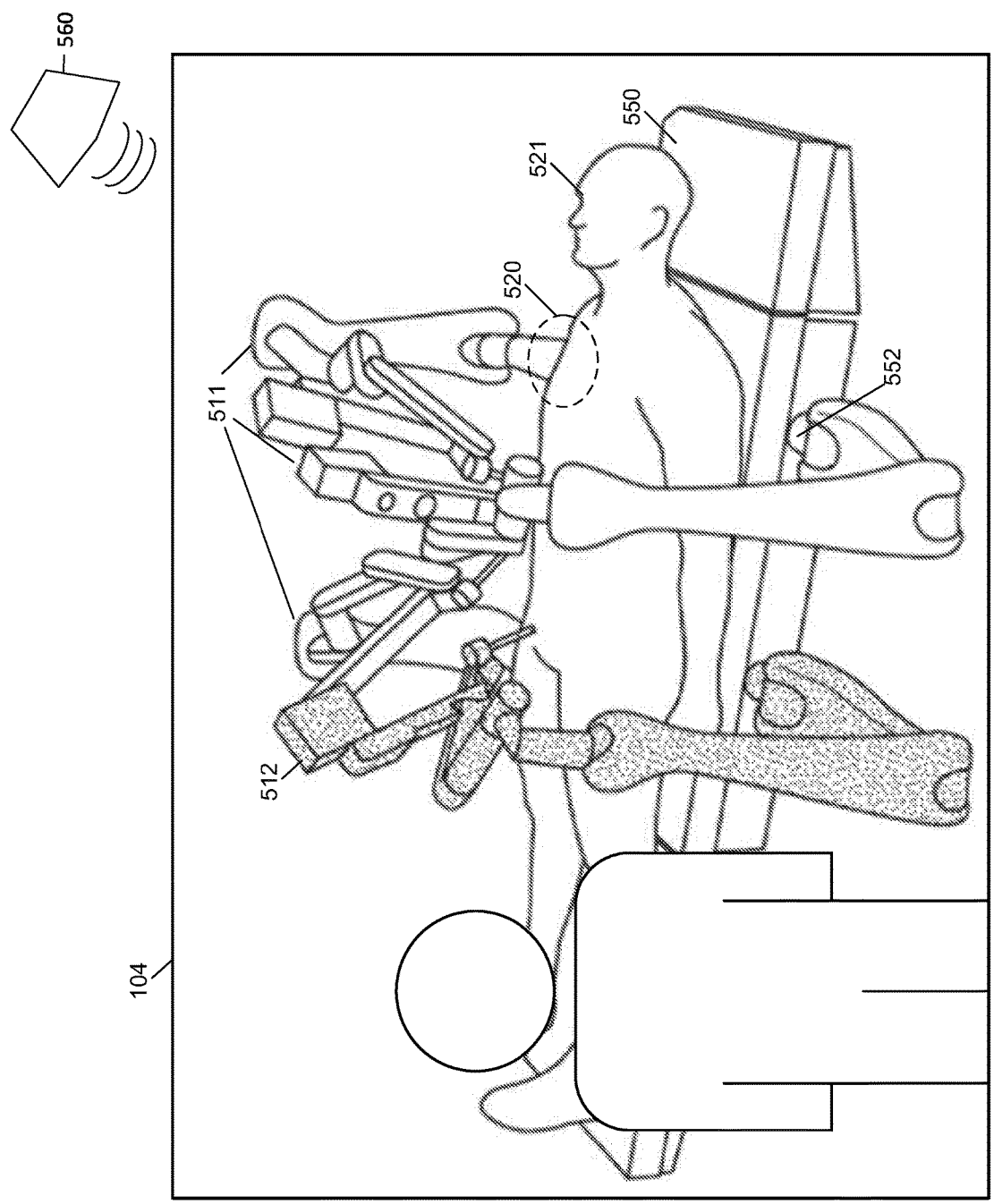
FIG. 5 illustrates indicators according to some embodiments.

Regarding such indications, FIG. 5 shows a display 104 that displays virtual surgical robotic arms 511 and 512 (note that the real robotic arms are omitted here to simplify the illustration, but would be present in practice). In this case, the processor has detected the pose of the real robotic arm is at the target pose of virtual surgical robotic arm 512. In response, the processor can trigger an indication, for example, a visual or audio indication, that the pose of the real surgical robotic arm is at the target pose.

For example, the AR processor can visually indicate that the real robotic arm is at the target pose by changing the color, brightness, transparency, or other visual attributes of the virtual robotic arm 512 (for example, rendering a bright outline around the virtual robotic arm).

In another embodiment, the indication can be a visual or text-based message on the display, generated by the AR processor, indicating that the target pose has been established. In another embodiment, the indication can be acoustic feedback, for example, a noise such as a beep or a voice, emanating from a speaker 560. In another embodiment, the indication can be haptic indication, for example, a vibration, generated by a vibrating actuator 112 of the robotic arm in the real surgical environment, as shown in FIG. 2. In another embodiment, the indication can be any combination of the visual, acoustic, or haptic indications described above.

Referring back to FIG. 1, in one embodiment, the AR processor can be configured to determine a zone 120 (as shown in FIG. 1) to be kept clear of objects (for example, lamps or other robotic arms), to allow for movements of the robotic arm during the operation, for example, based on predicting movements and travel of the robotic arm during the surgery, using a lookup table, or combinations thereof. The processor can be configured to display an indication of this zone (for example by rendering an outline of the zone) onto the augmented surgical environment video.

Cameras

In FIG. 1, the camera is shown as facing substantially in the same direction as the display. Beneficially, this provides a natural perspective and a direct view and line of site 107 to visually guide the user 106 in manipulating the surgical robotic arm 110. Alternatively, the camera can be strategically placed in other locations and orientations, capable of being determined based on routine experimentation and repetition.

Camera 140 can be a 2D camera, for example, a standard video camera or a standard digital video camera. The camera can alternatively be a 3D camera with depth sensing, for example, infrared, laser projection, multiple lenses (range imaging or stereo camera) or combinations thereof. The AR processor is configured to track a real surgical robotic arm and a surgical table and other objects in view, based on depth data received from the depth sensor and by comparing and matching objects in the surgical environment with 3D models of tables and robotics in computer memory. This helps perform collision detection and determine the pose of the real robotic arm.

The AR processor can determine relative depths of real objects and occlude virtual robotic arms with real objects, when the real objects are determined to be between the virtual robotic arms and the camera. For example, as shown in space 520 of FIG. 5, the processor can determine that the depth of the patient/dummy 521 is at a foreground compared a part of the virtual robotic arm 511, and occlude that part of the virtual robotic arm accordingly.

The system can include one or more additional cameras, the one or more additional cameras arranged and configured to capture different perspectives of the user setting up the robotic arm in the real surgical environment. In this case, the AR processor can be configured to receive the setup videos captured by the one or more additional cameras, render additional perspectives of the augmented surgical environment video for guiding the arm setup, and display one or more of the additional perspectives of the augmented surgical environment video.

Beneficially, by including multiple cameras, the AR processor can perform triangulation on the multiple perspectives to determine depths of objects in the surgical environment. Furthermore, the user can view the real and augmented robotic arm in multiple perspectives, thus providing an improved understanding of the visual space. The processor can be configured to display all of the one or more additional perspectives of the augmented surgical environment video on the display. Alternatively, the processor can select which of the perspectives to display, for example, based on a pose and/or position of the robotic arm, a position of the user, or a position of the user relative to the pose and/or position of the robotic arm, in the real surgical environment. For example, the processor can employ heuristics such as 'do not show a perspective where the robotic arm is blocked', or 'show perspective having best view of robotic arm or member of robotic arm being adjusted', or 'show perspective showing greatest change pose of the robotic arm'. The processor can determine and display the best perspective of the augmented surgical environment video, or provide a user interface for a user to select which of the perspectives to display, for example, on separate display or on the same display where the augmented video is shown. The augmented video can be shown, for example, on a display having a touch screen interface.

Collisions and Path Detection

Referring now to FIG. 3, the AR processor can be configured to determine a current pose of a real robotic arm 301 and calculate a path 304 between the current pose of the real robotic arm and the targeted pose of the virtual robotic arm 302; detect real objects 303 in the calculated path; and project on the captured surgical environment, visual indicators (for example, a message, an "X" or other symbol) that show one or more possible collisions between the real robotic arm and the real objects in the calculated path. For example, the processor can render an X on a lamp edge where the processor detects that the lamp edge will or may collide with the real robotic arm.

Pose Adjustments

In one embodiment, the AR processor can be configured to calculate a new target pose of the virtual robotic arms based on adjusting a saved pose (for example, one of the saved target poses in database 154 as shown in FIG. 2) of the virtual robotic arms. For example, the processor can adjust the target pose, automatically, based on a size of a patient, or based on an input from a user.

Referring back to FIG. 5, the AR processor can be configured to determine (for example, through computer vision) an orientation of a real surgical table 550 or other robotic mounting hardware 552, and adjust an orientation or pose (for example, the target pose) of the virtual robotic arm(s) (511 and 512) based on the orientation of the surgical table or other robotic mounting hardware.

Method

In one embodiment, a method for assisting robotic arm setup in a surgical robotic system using augmented reality can include capturing a live video of a user setting up a robotic arm in a surgical robotic system. The method can include rendering a visual guide representing a target pose of the robotic arm onto the live video, resulting in an augmented live video for guiding the arm setup, and displaying the augmented live video to the user. While the user is following the visual guide to set up the robotic arm, the method can include continuously processing the captured live video to determine whether the robotic arm has reached the target pose and notifying the user when the robotic arm has been set up at the target pose.

Figure 6:
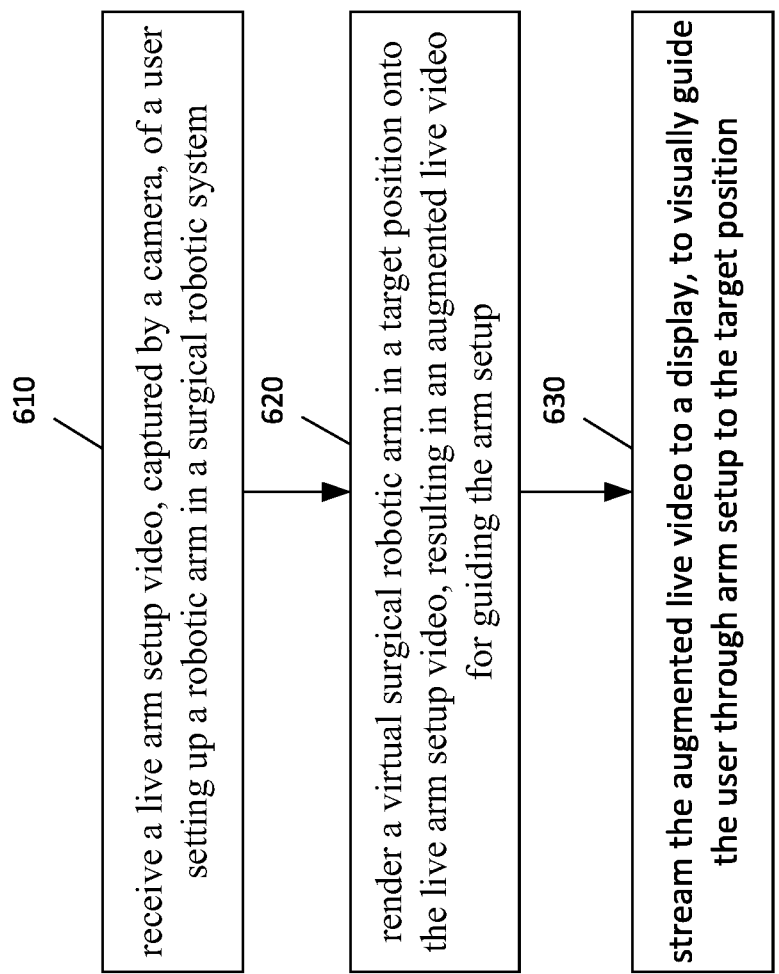
FIGS. 6-8 show methods performed by an AR processor in some embodiments.

Referring now to FIG. 6, in one embodiment, an AR processor can be configured to receive 610 an arm setup video, captured by a camera, of a user setting up the robotic arm in a real surgical environment. The processor can render 620 a virtual surgical robotic arm that is in a target pose, onto the arm setup video, resulting in an augmented surgical environment video for guiding the arm setup. The processor can then stream 630 the augmented video to a display, the display being configured to display the augmented surgical environment video.

Figure 7:
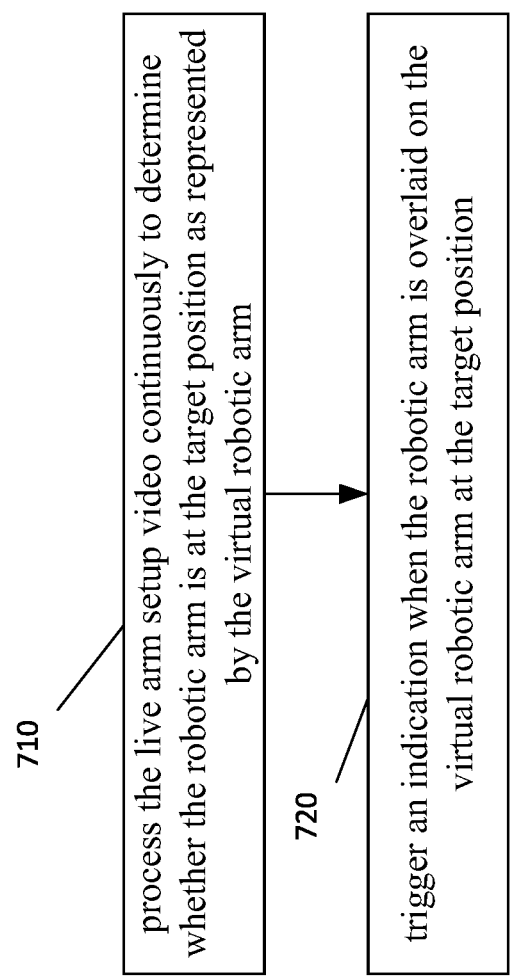

Referring now to FIG. 7 (showing features that can be additional to those of FIG. 6), the AR processor can also be also be configured to determine 710 whether a pose of a real surgical robotic arm is at the target pose of the virtual surgical robotic arm. The processor can trigger 720 an indication when the pose of the real surgical robotic arm is at, or overlaid upon, the virtual robotic arm.

Figure 8:
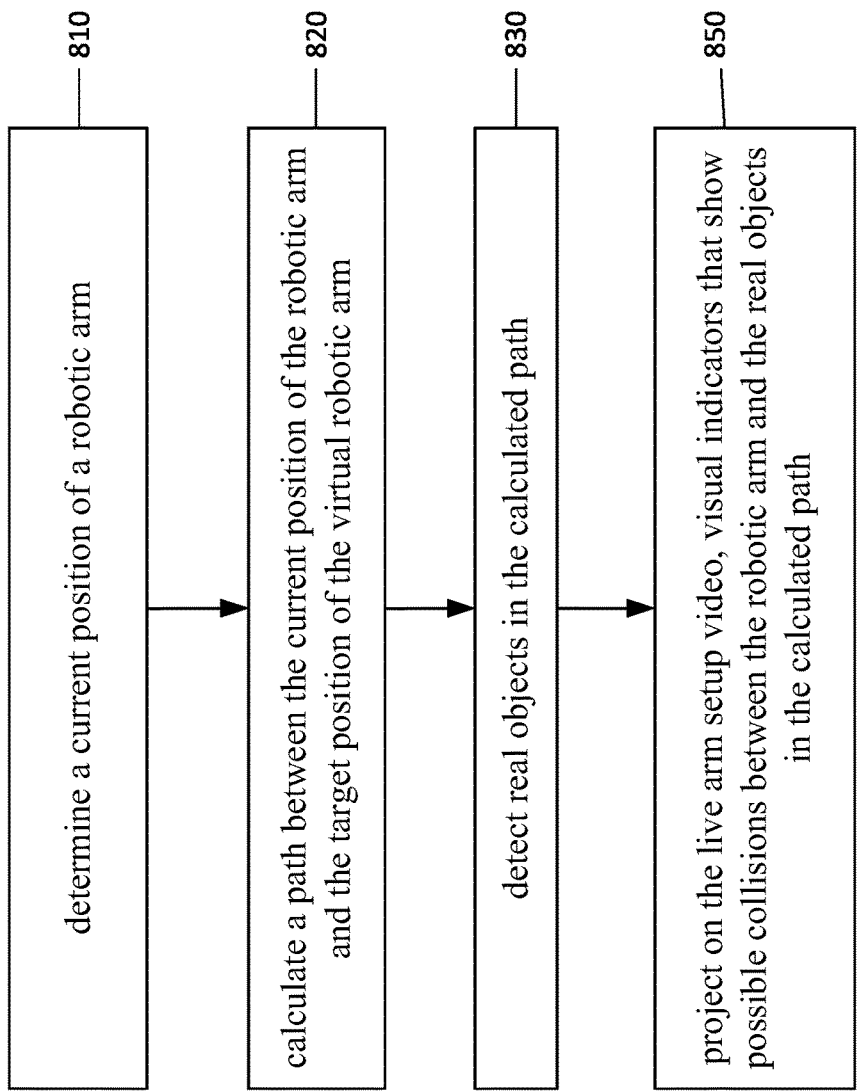

Referring now to FIG. 8 (showing features that can be additional to those of FIG. 6), the AR processor can also be configured to determine 810 a current pose of a real robotic arm, calculate 820 a path between the current pose of the robotic arm and the target pose of the virtual robotic arm, detect 830 real objects in the calculated path, and project/render 850 indicator(s) on the live arm setup video. The visual indictors can include, for example, a rendered arrow, and 'X', or other suitable graphics, showing possible collisions between the robotic arm and the real objects in the calculated path.

In one embodiment, the processors of the system (for example, the AR processor, processors in the cameras, displays, and robotic arms) can include a microprocessor and memory. Each processor may include a single processor or multiple processors with a single processor core or multiple processor cores included therein. Each processor may represent one or more general-purpose processors such as a microprocessor, a central processing unit (CPU), or the like. More particularly, each processor may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Each processor may also be one or more special-purpose processors such as an application specific integrated circuit (ASIC), a cellular or baseband processor, a field programmable gate array (FPGA), a digital signal processor (DSP), a network processor, a graphics processor, a communications processor, a cryptographic processor, a co-processor, an embedded processor, or any other type of logic capable of processing instructions.

Modules (for example, computer vision module 152), components and other features, such as algorithms or method steps described herein can be implemented by microprocessors, discrete hardware components or integrated in the functionality of hardware components such as ASICS, FPGAs, DSPs or similar devices. In addition, such features and components can be implemented as firmware or functional circuitry within hardware devices.

Note that while system 100 is illustrated with various components of a data processing system, it is not intended to represent any particular architecture or manner of interconnecting the components; as such details are not germane to embodiments of the present disclosure. It will also be appreciated that network computers, handheld computers, mobile computing devices, servers, and/or other data processing systems which have fewer components or perhaps more components may also be used with embodiments of the disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the disclosure also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present disclosure are not described with reference to any particular programming language. It will be appreciated that a variety of programming languages may be used to implement the teachings of embodiments of the disclosure as described herein.

In the foregoing specification, embodiments of the disclosure have been described with reference to specific exemplary embodiments thereof. It will be evident that various modifications may be made thereto without departing from the broader spirit and scope of the disclosure as set forth in the following claims. The specification and drawings are, accordingly, to be regarded in an illustrative sense rather than a restrictive sense. The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

What is claimed is:

1. A system for guiding arm setup in a surgical robotic system using augmented reality, comprising:
 a camera, configured to capture a live video of a user setting up a robotic arm in a surgical robotic system; and
 a processor, configured to:
 receive the live arm setup video captured by the camera;
 render a virtual surgical robotic arm in a target pose, onto the live arm setup video, resulting in an augmented live video for guiding the arm setup;
 stream the augmented live video as a mirror image to a display facing substantially in the same direction as the camera, to visually guide the user through arm setup to the target pose; and
 trigger an indication including at least one of a change in color or a change in transparency of the virtual robotic arm shown in the augmented live video on the display when the robotic arm is at, or within a tolerance of, the virtual robotic arm at the target pose.

2. The system according to claim 1, wherein the processor is further configured to
process the live arm setup video continuously to determine whether the robotic arm is at or within the tolerance of the target pose as represented by the virtual robotic arm.

3. The system according to claim 1, further comprising:
electronic memory having stored therein
one or more 3D models of robotic arms, each robotic arm being associated with one or more target poses, and
a user interface configured to provide selectable options of the one or more 3D models of robotic arms and the associated target poses.

4. The system according to claim 1, wherein the processor is configured to determine an orientation or position of a real surgical table or other robotic mounting hardware, and adjust the target pose of the virtual robotic arm based on the orientation or the position of the surgical table or other robotic mounting hardware.

5. The system, according to claim 1, wherein the processor is further configured to determine a current pose of the robotic arm;
calculate a path between the current pose of the robotic arm and the target pose of the virtual robotic arm;
detect real objects in the calculated path; and
project on the live arm setup video, visual indicators that show possible collisions between the robotic arm and the real objects in the calculated path.

6. The system according to claim 1, wherein the processor is configured to calculate a second target pose of the virtual robotic arm based on adjusting a saved pose of the virtual robotic arm with respect to a size of a patient.

7. The system according to claim 1, wherein the processor is configured to identify a robotic arm and a surgical table by comparing and matching objects in the surgical environment with 3D models of tables and robotics in computer memory.

8. The system according to claim 1, wherein the camera is a 2D camera.

9. The system according to claim 8, wherein the processor is configured to track a real surgical robotic arm and a surgical table with a 2D marker.

10. The system according to claim 1, wherein the camera is a 3D camera with a depth sensor.

11. The system according to claim 10, wherein the processor is configured to track a real surgical robotic arm and a surgical table and other objects in view, based on depth data received from the depth sensor and by comparing and matching objects in the surgical environment with 3D models of tables and robotics in computer memory.

12. The system according to claim 1, wherein the processor is configured to receive status from a real robotic arm in the real surgical environment.

13. The system according to claim 1, wherein the processor is configured to determine relative depths of real objects and occlude virtual robotic arms with real objects, when the real objects are determined to be between the camera and the virtual robotic arm.

14. The system according to claim 1, comprising:
one or more additional cameras, arranged to capture different perspectives of the user setting up the robotic arm in the real surgical environment; wherein the processor is configured to
receive one or more setup videos captured by the one or more additional cameras,
render one or more additional augmented surgical environment videos for guiding the arm setup, and
display one or more of the one or more of the additional augmented surgical environment videos to show different perspectives of the setting up of the robotic arm.

15. The system according to claim 14, wherein the processor is configured to display all of the one or more additional perspectives of the augmented surgical environment video.

16. The system according to claim 14, wherein the processor is configured to display a best perspective of the augmented surgical environment video.

17. The system according to claim 16, wherein the processor is configured to select which of the perspectives to display based on a location of the robotic arm, a location of the user, or a location of the user relative to the location of the robotic arm, in the real surgical environment.

18. A method for assisting robotic arm setup in a surgical robotic system using augmented reality, comprising:
capturing, with a camera, a live video of a user setting up a robotic arm in a surgical robotic system;
rendering a visual guide representing a target pose of the robotic arm onto the live video, resulting in an augmented live video for guiding the arm setup;
displaying the augmented live video to the user as a mirror image on a display facing substantially in a same direction as the camera;
while the user is following the visual guide to set up the robotic arm, continuously processing the captured live video to determine whether the robotic arm has reached the target pose; and
triggering an indication including at least of a change in color or a change in transparency of the virtual robotic arm shown in the augmented live video on the display when the robotic arm is at, or within a tolerance of, the virtual robotic arm at the target pose.

19. A system for guiding arm setup in a surgical robotic system using augmented reality, comprising:
a camera, configured to capture a live video of a user setting up a robotic arm in a surgical robotic system; and
a processor, configured to:
receive the live arm setup video captured by the camera;
render a virtual surgical robotic arm in a target pose, onto the live arm setup video, resulting in an augmented live video for guiding the arm setup;
calculate a path between a current pose of the robotic arm and the target pose of the virtual robotic arm;
stream the augmented live video as a mirror image to a display facing substantially in the same direction as the camera, to visually guide the user through arm setup to the target pose; and
trigger an indication shown in the augmented live video on the display when a) the robotic arm is at, or within a tolerance of, the virtual robotic arm at the target pose, and b) a possible collision is detected between the robotic arm and a real object in the calculated path.

* * * * *